United States Patent
Wegner et al.

(10) Patent No.: US 8,530,524 B2
(45) Date of Patent: *Sep. 10, 2013

(54) FOAMING ALCOHOL COMPOSITIONS WITH SELECTED DIMETHICONE SURFACTANTS

(71) Applicant: Ecolab USA Inc., St. Paul, MN (US)

(72) Inventors: Joseph R. Wegner, Falcon Heights, MN (US); Cheryl A. Littau, Apple Valley, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/742,996

(22) Filed: Jan. 16, 2013

(65) Prior Publication Data

US 2013/0137777 A1    May 30, 2013

Related U.S. Application Data

(63) Continuation of application No. 13/223,419, filed on Sep. 1, 2011, now Pat. No. 8,383,686, which is a continuation of application No. 12/787,624, filed on May 26, 2010, now Pat. No. 8,058,315, which is a continuation of application No. 12/179,382, filed on Jul. 24, 2008, now Pat. No. 7,842,725.

(51) Int. Cl.
*A61K 31/045* (2006.01)
*A61K 31/74* (2006.01)
*A01N 25/34* (2006.01)

(52) U.S. Cl.
USPC ............ 514/724; 424/78.03; 424/78.07; 424/404

(58) Field of Classification Search
USPC .............. 514/724; 424/78.03, 78.07, 404
See application file for complete search history.

(56) References Cited

U.S. PATENT DOCUMENTS

| | | |
|---|---|---|
| 3,787,566 A | 1/1974 | Gauvreau et al. |
| 4,220,665 A | 9/1980 | Klein |
| 4,336,151 A | 6/1982 | Like et al. |
| 4,511,486 A | 4/1985 | Shah |
| 4,714,568 A | 12/1987 | Hurnik et al. |
| 4,857,302 A | 8/1989 | Decker et al. |
| 5,015,228 A | 5/1991 | Columbus et al. |
| 5,047,249 A | 9/1991 | Rothman et al. |
| 5,073,371 A | 12/1991 | Turner et al. |
| 5,167,950 A | 12/1992 | Lins |
| D338,585 S | 8/1993 | Bell |
| 5,256,401 A | 10/1993 | Duckenfield |
| 5,265,772 A | 11/1993 | Bartasevich |
| 5,266,598 A | 11/1993 | Ninomiya et al. |
| D343,751 S | 2/1994 | Bell |
| D346,332 S | 4/1994 | Kanfer |
| 5,336,497 A | 8/1994 | Guerrero et al. |
| 5,370,267 A | 12/1994 | Schroeder |
| 5,441,178 A | 8/1995 | Wysocki |
| 5,443,236 A | 8/1995 | Bell |
| 5,449,137 A | 9/1995 | Bell |
| 5,462,688 A | 10/1995 | Lippman |
| D365,509 S | 12/1995 | Bell |
| D365,518 S | 12/1995 | Wysocki |
| D365,755 S | 1/1996 | Kanfer |
| 5,523,014 A | 6/1996 | Dolan |
| 5,558,453 A | 9/1996 | Bell |
| 5,587,358 A | 12/1996 | Sukigara |
| 5,625,659 A | 4/1997 | Sears |
| 5,629,006 A | 5/1997 | Hoang et al. |
| 5,635,462 A | 6/1997 | Fendler |
| D383,001 S | 9/1997 | Bell |
| D385,795 S | 11/1997 | Wysocki |
| 5,718,353 A | 2/1998 | Kanfer |
| 5,719,113 A | 2/1998 | Fendler |
| D392,136 S | 3/1998 | Ross |
| 5,725,131 A | 3/1998 | Bell et al. |
| D400,799 S | 11/1998 | Bell |
| 5,902,778 A | 5/1999 | Hartmann et al. |
| D411,456 S | 6/1999 | Mast |
| 5,944,227 A | 8/1999 | Schroeder |
| D415,343 S | 10/1999 | Maddox |
| 5,972,356 A | 10/1999 | Peffly et al. |
| D416,417 S | 11/1999 | Ross |
| 5,996,851 A | 12/1999 | Dolan |
| D418,708 S | 1/2000 | Kanfer |

(Continued)

FOREIGN PATENT DOCUMENTS

| | | |
|---|---|---|
| DE | 19523320 | 1/1997 |
| EP | 0849070 | 6/1998 |
| EP | 0882446 | 12/1998 |
| WO | WO 2005/051341 | 6/2005 |
| WO | WO 2006/094387 A1 | 9/2006 |

OTHER PUBLICATIONS

Brehm-Stecher, Johnson, "Sensitization of *Staphylococcus aureus* and *Escherichia coli* to Antibiotics by the Sesquiterpenoids Nerolidol, Farnesol, Bisabolol, and Apritone", University of Wisconsin—Madison, Antimicrobial Agents and Chemotherapy, Oct. 2003, vol. 47, No. 10, p. 3357-3360, 4 pages.
Cosmocil(TM) Folder, 5 pages.
Intrinsic Activity of Cosmocil CQ, Avecia, 2 pages.
Morton, H., "The relationship of concentration and germicidal efficiency of ethyl alcohol.", Annals of the New York Academy of Sciences, vol. 52, 1950, pp. 191-196, XP008066591, the whole document.
Schloss Man, M. (Ed.): "The chemistry and manufacture of cosmetics: formulating. vol. 2, Ed. 3", 2000, Allured Pub., USA 277870, XP002390779, p. 237.

(Continued)

*Primary Examiner* — Raymond Henley, III
(74) *Attorney, Agent, or Firm* — McKee, Voorhees & Sease, P.L.C.

(57) ABSTRACT

Foaming alcohol compositions with selected dimethicone surfactants are disclosed. The dimethicone surfactants are PEG-8 to PEG-12 linear dimethicone surfactants and in particular PEG-10 linear dimethicone surfactant. The compositions are useful as antimicrobial products and in particular handcare or skincare products.

17 Claims, No Drawings

(56) References Cited

U.S. PATENT DOCUMENTS

| | | |
|---|---|---|
| 6,022,551 A | 2/2000 | Jampani et al. |
| D422,828 S | 4/2000 | Kanfer |
| 6,065,639 A | 5/2000 | Maddox |
| 6,090,395 A | 7/2000 | Asmus |
| 6,130,253 A | 10/2000 | Franklin et al. |
| 6,183,766 B1 | 2/2001 | Sine et al. |
| 6,217,885 B1 | 4/2001 | Roder et al. |
| 6,265,363 B1 | 7/2001 | Viscovitz |
| 6,267,976 B1 | 7/2001 | Barnhart |
| 6,274,124 B1 | 8/2001 | Vollhardt |
| 6,319,958 B1 | 11/2001 | Johnson et al. |
| 6,333,039 B1 | 12/2001 | Fendler |
| 6,352,701 B1 | 3/2002 | Scholz et al. |
| 6,383,505 B1 | 5/2002 | Kaiser |
| 6,383,997 B1 | 5/2002 | McManus |
| 6,423,329 B1 | 7/2002 | Sine |
| 6,534,069 B1 | 3/2003 | Asmus |
| 6,592,880 B1 | 7/2003 | Jager |
| 6,689,593 B2 | 2/2004 | Millis |
| 6,709,647 B2 | 3/2004 | Bhakoo |
| 6,723,689 B1 | 4/2004 | Hoang |
| 6,846,846 B2 | 1/2005 | Modak et al. |
| 6,977,082 B2 | 12/2005 | Seitz, Jr. et al. |
| 7,166,435 B2 | 1/2007 | Rosenbloom |
| 7,199,090 B2 | 4/2007 | Koivisto et al. |
| 7,842,725 B2 | 11/2010 | Wegner et al. |
| 8,058,315 B2 | 11/2011 | Wegner et al. |
| 8,383,686 B2* | 2/2013 | Wegner et al. ............. 514/724 |
| 2002/0022660 A1 | 2/2002 | Jampani |
| 2004/0102429 A1 | 5/2004 | Modak et al. |
| 2004/0191274 A1 | 9/2004 | Grayson et al. |
| 2004/0247685 A1 | 12/2004 | Modak et al. |
| 2006/0104911 A1 | 5/2006 | Novak |
| 2006/0104919 A1 | 5/2006 | Novak |
| 2006/0182690 A1 | 8/2006 | Veeger et al. |
| 2006/0281663 A1 | 12/2006 | Asmus |
| 2007/0027055 A1 | 2/2007 | Koivisto et al. |
| 2007/0065383 A1 | 3/2007 | Fernandez De Castro et al. |
| 2007/0148101 A1 | 6/2007 | Snyder et al. |
| 2007/0179207 A1 | 8/2007 | Fernandez De Castro et al. |
| 2007/0258911 A1 | 11/2007 | Fernandez De Castro et al. |

OTHER PUBLICATIONS

Technical Information from BASF for Bisabolol, Nov. 2002, 8 pages.
Technical Specification for Farnesol, Symrise, Jun. 1, 2004, 2 pages.
Search Report for co-pending PCT/IB2009/052871 listing relevant art cited by the International Searching Authority, (2009).
Worldwide Healthcare Inc., "Material Safety Data Sheet", Jan. 24, 2007.

* cited by examiner

FOAMING ALCOHOL COMPOSITIONS WITH SELECTED DIMETHICONE SURFACTANTS

CROSS-REFERENCE TO RELATED APPLICATIONS

This application is a Continuation application of U.S. Ser. No. 13/223,419 filed Sep. 1, 2011, now U.S. Pat. No. 8,383,686 issued on Feb. 26, 2013, which is a Continuation application of U.S. Ser. No. 12/787,624, filed May 26, 2010, now U.S. Pat. No. 8,058,315 issued on Nov. 15, 2011, which is a Continuation of U.S. Ser. No. 12/179,382 filed Jul. 24, 2008, now U.S. Pat. No. 7,842,725, issued Nov. 30, 2010, herein incorporated by reference in their entirety.

FIELD OF THE INVENTION

Foaming alcohol compositions with selected dimethicone surfactants are disclosed. The dimethicone surfactants are PEG-8 to PEG-12 linear dimethicone surfactants and in particular PEG-10 linear dimethicone surfactant. The compositions are useful as antimicrobial products and in particular handcare or skincare products.

BACKGROUND

Alcohol compositions are desirable hand and skincare products. They are effective against a wide range of microorganisms such as gram positive and gram negative bacteria and fungi. And they are able to kill microorganisms faster than other antimicrobial products. Alcohol antimicrobial products are available as water thin liquids, gels, emulsions, and aerosol foams. Commercially available aerosol alcohol foams, such as QUIKCARE™, commercially available from Ecolab Inc. (St. Paul, Minn.) rely on propellants to generate the foam. Propellants are needed because the surface tension of alcohol is too low for most surfactants to be able to generate foam and sustain it at atmospheric pressure. But, aerosol products are less desirable because of their inherent drawbacks of not being able to visually monitor the product contents in the container, the additional packaging complexity, and cost. It is desirable to move away from aerosol cans and aerosol propellants to less complex packaging and chemistry that allows a customer to see the product contents in the container while maintaining the aesthetic benefits of a foaming product. It is against this background that the present invention has been made.

SUMMARY

Surprisingly, it has been discovered that PEG-8 to PEG-12 linear dimethicone surfactants and in particular PEG-10 linear dimethicone surfactant are especially effective at generating foam in alcohol products at atmospheric pressure in transparent or translucent, non-aerosol packaging. The PEG-8 to PEG-12 linear dimethicone surfactants are more effective than dimethicone surfactants with the same PEG chain length but a different polymer architecture.

In some embodiments, the invention relates to a non-aerosol antimicrobial composition with a PEG-8 to PEG-12 linear dimethicone surfactant, an alcohol, and water, where the dimethicone can generate an average foam height of greater than 20 mm without needing more than 5% of additional surfactant. In some embodiments, the invention relates to a non-aerosol antimicrobial composition with a PEG-10 linear dimethicone surfactant, an alcohol, and water, where the dimethicone can generate an average foam height of greater than 20 mm without needing more than 5% of additional surfactant. In some embodiments, the composition also contains additional materials such as skin conditioners, terpenoids, chelating agents, and preservatives.

These and other embodiments will be apparent to those of skill in the art and others in view of the following detailed description of some embodiments. It should be understood, however, that this summary, and the detailed description illustrate only some examples of various embodiments, and are not intended to be limiting to the invention as claimed.

DETAILED DESCRIPTION OF SOME EMBODIMENTS

As discussed above, the invention generally relates to foaming alcohol compositions with PEG-8 to PEG-12 linear dimethicone surfactants and in particular PEG-10 linear dimethicone surfactant. The compositions are useful as antimicrobial products and in particular handcare or skincare products.

PEG-8 to PEG-12 Linear Dimethicone Surfactants

Surprisingly, it has been discovered that PEG-8 to PEG-12 linear dimethicone surfactants, and in particular PEG-10 linear dimethicone surfactant, are more effective at generating and stabilizing foam in alcohol compositions than dimethicone surfactants with the same PEG chain length but a different polymer architecture.

More particularly it has been discovered that linear block copolymers of PEG with polydimethylsiloxane (specifically with INCI names of PEG-8 dimethicone, PEG-10 dimethicone, and PEG-12 dimethicone) can produce a sufficient foam height to be used as the primary foaming component of a non-aerosol foaming alcohol compositions, which is not the case for copolymers with the same INCI names but different polymer architectures. For example, polymers with pendant PEG groups or other highly branched polymer structures, will not produce sufficient foam to be used as a primary foaming surfactant. In the case of PEG dimethicone copolymers, linear block copolymers refer to when polyethylene glycol chain units are attached to the terminal ends of the linear polydimethylsiloxane backbone:

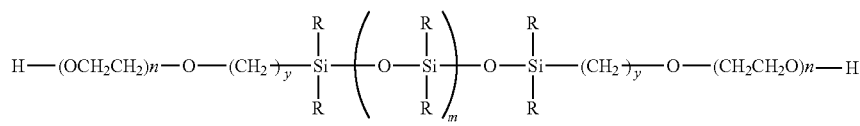

where R=CH$_3$ or CH$_2$CH$_3$, m=4-20 on average, y=1-5 and n=8-12 on average.

Pendant copolymers refer to linear polydimethylsiloxane polymers with PEG groups attached along the polydimethylsiloxane backbone and may or may not be attached to the terminal chain ends of the polydimethylsiloxane. Such pendant copolymers are often referred to as having a comb or comb-like structure such as:

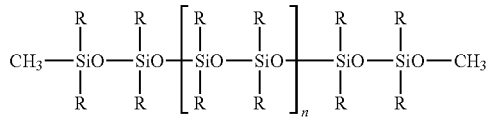

where R is independently=CH$_3$, CH$_2$CH$_3$, or an ethoxylated alkyl chain (for example CH$_2$CH$_2$CH$_2$O(CH$_2$CH$_2$O)$_n$H) attached directly to the silicone end group and a=a repeating silicone group.

Some examples of commercially available PEG-8 to PEG-12 linear dimethicone surfactants include Silsoft 810 (PEG-8) and Silsoft 870 (PEG-12) from Momentive Performance Materials, and Silsurf DI-1010 (PEG-10) from Siltech. In some embodiments, the dimethicone surfactant is preferably a PEG-10 linear dimethicone surfactant.

The dimethicone surfactant can be present in the alcohol composition from about 0.5 to about 10 wt. %, from about 1.0 to about 7 wt. % and from about 2 to about 5 wt. %.

Alcohol

In addition to water, the composition includes an alcohol. The alcohol is preferably a lower chain alcohol such as a C$_2$-C$_4$ alcohol. Examples of suitable alcohols include ethanol, propanols, such as isopropanol and n-propanol, and butanols. The alcohol is preferably ethanol.

The composition may contain one alcohol, or a mixture of two or more alcohols. The alcohol is preferably present in the composition in an amount of active alcohol from about 50 to about 90 wt. %, from about 54 to about 85 wt. %, and from about 60 to about 80 wt. %.

Skin Conditioner

The composition may optionally include at least one skin conditioner such as an emollient, humectant, occlusive agent, or other moisturizer to provide moisturization, skin softening, skin barrier maintenance, anti-irritation, or other skin health benefits. Some non-limiting examples of emollients include alkyl benzoate, myristyl myristate, cetyl myristate, glyceryl dioleate, methyl laurate, PPG-9 laurate, lauryl lacylate allantoin, octyl palmitate, lanolin, propylene glycol, butylenes glycol, ethylene glycol monobutyl ether, glycerine, fatty acids, natural oils such as almond, mineral, canola, sesame, soybean, wheat germ, corn, peanut and olive oil, isopropyl myristate, myristyl alcohol, aloe vera, hydrolyzed silk protein, Vitamin E, stearyl alcohol, isopropyl palmitate, sorbitol, amino acid complexes, hydrolyzed plant proteins, and polyethylene glycol. Some non-limiting examples of humectants include hydroxyethyl urea, agarose, urea, sodium PCA, arginine PCA, fructose, glucose, glutamic acid, glycerine, honey, lactose, maltose, polyethylene glycol, sorbitol and mixtures thereof. Some non-limiting examples of occlusive agents include petrolatum, shea butter, avocado oil, balm mint oil, cod liver oil, mineral oil, trimyristin, stearyl stearate, synthetic wax, or mixtures thereof. Some non-limiting examples of other moisturizers include ethyl hexylglycerin, cholesterol, cystine, hyaluronic acid, keratin, lecithin, egg yolk, glycine, PPG-12, polyquaternium polymers such as polyquaternium-11, benentrimonium chloride, dihydroxypropyl PEG-5 linoleammonium chloride, glycerol oleate, PEG-7 glyceryl cocoate, cocoglucoside, PEG-200 hydrogenated glyceryl palmate, panthenol, retinol, salicylic acid, vegetable oil, methyl gluceth-10, methyl gluceth-20, ethoxylated derivatives of skin conditioners such as glycereth-26 and ethoxylated shea butter, and mixtures thereof. Finally, some non-limiting examples of anti-irritants include bisabolol and panthenol.

A person skilled in the art will recognize the different strengths of different skin conditioners and formulate accordingly. In some embodiments, the skin conditioner is preferably present in the composition in an amount from about 0.01 to about 20 wt. %, from about 0.05 to about 15 wt. %, and from about 0.1 to about 10 wt. %.

Terpenoid

The composition may optionally include a terpenoid. Terpenoids are defined as materials with molecular structures containing carbon backbones made up of isoprene (2-methylbuta-1,3-diene) units. Isoprene contains five carbon atoms and therefore, the number of carbon atoms in any terpenoid is a multiple of five. It is believed that terpenoids assist in promoting the uptake of antimicrobial compounds and preservatives by cells of bacteria and fungi, thereby increasing the efficacy of the antimicrobial compound or preservative. See U.S. Pat. No. 6,319,958 and DE 195 23 320 which are incorporated by reference in their entirety. Some non-limiting examples of terpenoids include α-terpinene, cineole, citral, citronellal, citronellol, farnesol, geraniol, limonene, linalool, methone, nerolidol, terpineol, camphene, menthone, myrcene, nerol, tetrayhydrogeraniol, tetrahydrolinalool, apritone, and bisabolol. The terpenoid is preferably farnesol, nerolidol, bisabolol, or apritone.

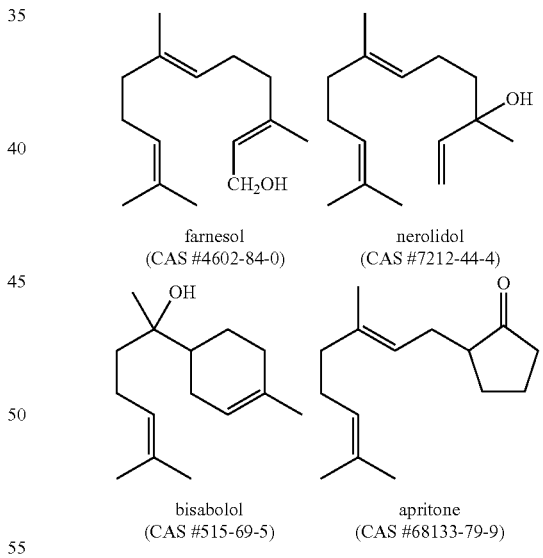

The terpenoid is preferably present in the composition in an amount from about 0.005 to about 5 wt. %, from about 0.05 to about 2.5 wt. %, and from about 0.1 to about 1.5 wt. %.

Chelating Agent

The composition may optionally include a chelating agent. Examples of chelating agents include phosphonic acid and phosphonates, phosphates, aminocarboxylates and their derivatives, pyrophosphates, ethylenediamine and ethylenetriamine derivatives, hydroxyacids, and mono-, di-, and tricarboxylates and their corresponding acids. Other chelating agents include nitroloacetates and their derivatives, and mixtures thereof. Examples of aminocarboxylates include amino acetates and salts thereof. Suitable amino acetates include: N-hydroxyethylaminodiacetic acid; hydroxyethylenediaminetetraacetic acid; nitrilotriacetic acid (NTA); ethylenediaminetetraacetic acid (EDTA); N-hydroxyethyl-ethylenediaminetriacetic acid (HEDTA); tetrasodium ethylenediaminetetraacetic acid (EDTA); diethylenetriaminepentaacetic acid (DTPA); and alanine-N,N-diacetic acid; n-hydroxyethyliminodiacetic acid; and the like; their alkali metal salts; and mixtures thereof. Suitable aminophosphates include nitrilotrismethylene phosphates and other aminophosphates with alkyl or alkaline groups with less than 8 carbon atoms. Exemplary polycarboxylates iminodisuccinic acids (IDS), sodium polyacrylates, citric acid, gluconic acid, oxalic acid, salts thereof, mixtures thereof, and the like. Additional polycarboxylates include citric or citrate-type chelating agents, polymeric polycarboxylate, and acrylic or polyacrylic acid-type chelating agents. Additional chelating agents include polyaspartic acid or co-condensates of aspartic acid with other amino acids, $C_4$-$C_{25}$-mono-or-dicarboxylic acids and $C_4$-$C_{25}$-mono-or-diamines. Exemplary polymeric polycarboxylates include polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, and the like.

The chelating agent may be present in an amount from about 0.01 to about 5 wt. %, from about 0.05 to about 3 wt. %, and from about 0.1 to about 1.5 wt. %.

Preservatives

The composition may optionally include a preservative. Generally, preservatives fall into specific classes including phenolics, halogen compounds, quaternary ammonium compounds, metal derivatives, amines, alkanolamines, nitro derivatives, biguanides, analides, organosulfur and sulfur-nitrogen compounds, alkyl parabens, and miscellaneous compounds. Some non-limiting examples of phenolic antimicrobial agents include pentachlorophenol, orthophenylphenol, chloroxylenol, p-chloro-m-cresol, p-chlorophenol, chlorothymol, m-cresol, o-cresol, p-cresol, isopropyl cresols, mixed cresols, phenoxyethanol, phenoxyethylparaben, phenoxyisopropanol, phenyl paraben, resorcinol, and derivatives thereof. Some non-limiting examples of halogen compounds include trichlorohydroxy diphenyl ether (Triclosan), sodium trichloroisocyanurate, sodium dichloroisocyanurate, iodine-poly(vinylpyrolidin-onen) complexes, and bromine compounds such as 2-bromo-2-nitropropane-1,3-diol, and derivatives thereof. Some non-limiting examples of quaternary ammonium compounds include benzalkonium chloride, benzethonium chloride, behentrimonium chloride, cetrimonium chloride, and derivatives thereof. Some non-limiting examples of amines and nitro containing compounds include hexahydro-1,3,5-tris(2-hydroxyethyl)-s-triazine, dithiocarbamates such as sodium dimethyldithiocarbamate, and derivatives thereof. Some non-limiting examples of biguanides include polyaminopropyl biguanide and chlorhexidine gluconate. Some non-limiting examples of alkyl parabens include methyl, ethyl, propyl and butyl parabens.

The preservative is preferably present in the composition in an amount from about 0 to about 3 wt. %, from about 0.1 to about 2 wt. %, and from about 0.2 to about 1 wt. %.

Thickener

The composition may optionally include a thickener. Exemplary thickeners include (1) cellulosic thickeners and their derivatives, (2) natural gums, (3) starches, (4) stearates, and (5) fatty acid alcohols. Some non-limiting examples of cellulosic thickeners include carboxymethyl hydroxyethylcellulose, cellulose, hydroxybutyl methylcellulose, hydroxyethylcellulose, hydroxypropylcellulose, hydroxypropyl methyl cellulose, methylcellulose, microcrystalline cellulose, sodium cellulose sulfate, and the like. Some non-limiting examples of natural gums include acacia, calcium carrageenan, guar, gelatin, guar gum, hydroxypropyl guar, karaya gum, kelp, locust bean gum, pectin, sodium carrageenan, tragacanth gum, xanthan gum, and the like. Some non-limiting examples of starches include oat flour, potato starch, wheat flour, wheat starch, and the like. Some non-limiting examples of stearates include PEG-150 distearate, methoxy PEG-22/dodecyl glycol copolymer, and the like. Some non-limiting examples of fatty acid alcohols include caprylic alcohol, cetearyl alcohol, lauryl alcohol, oleyl alcohol, palm kernel alcohol, and the like.

The amount of thickener in the composition depends on the desired viscosity of the composition. The composition preferably has a viscosity low enough to pump through a foamer such as an Airspray foamer and allow foaming.

Additional Functional Ingredients

Additional functional ingredients may be used to improve the effectiveness of the composition. Some non-limiting examples of such additional functional ingredients include skin feel improvers, antioxidants, fragrances, dyes, and mixtures thereof.

Skin Feel Improver

The composition may optionally include a skin feel improver for enhancing the "feel" of the composition on a user's skin or hands. For example, it may be undesirable for a composition to have a scaly or gritty texture when applied to a user's skin or after the multiple applications of the composition. Some non-limiting examples of skin feel improvers include silicone copolymers such as amodimethicone, cyclomethicone, bis-PEG/PPG-20/20 dimethicone, and stearoxytrimethylsilane, naturally occurring or synthetic fatty acid esters or ethers, and polyalkylene glycols.

If a skin feel improver is included, it is preferably present in the composition in an amount from about 0.001 to about 5 wt. %, from about 0.01 to about 3 wt. %, and from about 0.1 to about 2 wt. %.

Antioxidant

The composition may optionally include an antioxidant for improved skin condition through the removal of free radicals, and improved product stability. Some non-limiting examples of antioxidants include retinol and retinol derivatives, ascorbic acid and ascorbic acid derivatives, BHA, BHT, betacarotene, cysteine, erythorbic acid, hydroquinone, tocopherol and tocopherol derivatives, and the like.

If an antioxidant is included, it is preferably present in the composition in an amount from about 0.001 to about 2 wt. %, from about 0.01 to about 1 wt. %, and from about 0.05 to about 0.5 wt. %.

Fragrance

The composition may optionally include a fragrance. Examples of possible fragrances include natural oils or naturally derived materials, and synthetic fragrances such as hydrocarbons, alcohols, aldehydes, ketones, esters, lactones, ethers, nitriles, and polyfunctionals. Non-limiting examples of natural oils include the following: basil (*Ocimum basilicum*) oil, bay (*Pimento acris*) oil, bee balm (*Monarda didyma*) oil, bergamot (*Citrus aurantium bergamia*) oil, cardamom (*Elettaria cardamomum*) oil, cedarwood (*Cedrus atlantica*) oil, chamomile (*Anthemis nobilis*) oil, cinnamon (*Cinnamomum cassia*) oil, citronella (*Cymbopogon nardus*) oil, clary (*Salvia sclarea*) oil, clove (*Eugenia caryophyllus*)

oil, cloveleaf (*Eufenia caryophyllus*) oil, *Cyperus esculentus* oil, cypress (*Cupressus sempervirens*) oil, *Eucalyptus citriodora* oil, geranium maculatum oil, ginger (*Zingiber officinale*) oil, grapefruit (*Citrus grandis*) oil, hazel (*Corylus avellana*) nut oil, jasmine (*Jasminum officinale*) oil, *Juniperus communis* oil, *Juniperus oxycedrus* tar, *Juniperus virginiana* oil, kiwi (*Actinidia chinensis*) water, lavandin (*Lavandula hybrida*) oil, lavender (*Lavandula angustifolia*) oil, lavender (*Lavandula angustifolia*) water, lemon (*Citrus medica limonum*) oil, lemongrass (*Cymbopogon schoenanthus*) oil, lime (*Citrus aurantifolia*) oil, linden (*Tilia cordata*) oil, linden (*Tilia cordata*) water, mandarin orange (*Citrus nobilis*) oil, nutmeg (*Myristica fragrans*) oil, orange (*Citrus aurantium dulcis*) flower oil, orange (*Citrus aurantium dulcis*) oil, orange (*Citrus aurantium dulcis*) water, patchouli (*Pogostemon cablin*) oil, peppermint (*Menthe piperita*) oil, peppermint (*Menthe peperita*) water, rosemary (*Rosmarinus officinalis*) oil, rose oil, rose (*Rosa damascena*) extract, rose (*Rosa multiflora*) extract, rosewood (*Aniba rosaeodora*) extract, sage (*Salvia officinalis*) oil, sandalwood (*Santalum album*) oil, spearmint (*Menthe viridis*) oil, tea tree (*Melaleuca alternifolia*) oil, and ylang ylang (*Cananga odorata*) oil. Some non-limiting examples of synthetic hydrocarbon fragrances include caryophyllene, β-farnesene, limonene, α-pinene, and β-pinene. Some non-limiting examples of synthetic alcohol fragrances include bacdanol, citronellol, linalool, phenethyl alcohol, and α-terpineol (R=H). Some non-limiting examples of synthetic aldehyde fragrances include 2-methyl undecanal, citral, hexyl cinnamic aldehyde, isocycolcitral, lilial, and 10-undecenal. Some non-limiting examples of synthetic ketone fragrances include cashmeran, α-ionone, isocyclemone E, koavone, muscone, and tonalide. Some non-limiting examples of synethetic ester fragrances include benzyl acetate, 4-t-butylcyclohexyl acetate (cis and trans), cedryl acetate, cyclacet, isobornyl acetate, and α-terpinyl acetate (R=acetyl). Some non-limiting examples of synthetic lactone fragrances include coumarin, jasmine lactone, muskalactone, and peach aldehyde. Some non-limiting examples of synthetic ether fragrances include ambroxan, anther, and galaxolide. Some non-limiting examples of synthetic nitrile fragrances include cinnamonitrile and gernonitrile. Finally, some non-limiting examples of synthetic polyfunctional fragrances include amyl salicylate, isoeugenol, hedione, heliotropine, lyral, and vanillin.

The composition may include a mixture of fragrances including a mixture of natural and synthetic fragrances. The fragrance can be present in a composition in an amount up to about 5 wt. %, preferably from about 0.01 to about 3 wt. %, from about 0.05 to about 1 wt. %, and from about 0.1 to about 0.2 wt. %.

Dye

The composition may optionally include a dye. Examples of dyes include any water soluble or product soluble dye, any FD&C or D&C approved dye. The dye can be present in an amount up to about 0.5 wt. %, preferably from about 0.00001 to about 0.1 wt. %, from about 0.0001 to about 0.01 wt. %, and from about 0.0001 to about 0.0005 wt. %.

Compositions

The non-aerosol alcohol compositions are especially useful as hand and skincare compositions for reducing microorganisms on the target surface.

In some embodiments, the composition includes less than about 10%, less than about 5% or less than about 1% any additional surfactant. The use of additional surfactant may be limited because the selected dimethicone surfactants are capable of producing and maintaining foam without needing help from additional surfactants.

In some embodiments, the composition includes less than about 10%, less than about 5% or less than about 1% any additional silicone materials besides the PEG-8, PEG-10, or PEG-12 linear dimethicone surfactant.

In some embodiments, the composition includes less than about 10%, less than about 5% or less than about 1% any foam stabilizers.

In some embodiments, the composition may be free or substantially free of additional surfactant, additional silicone material, or foam stabilizer. In some embodiments, the composition may be free or substantially free of a fluorosurfactant.

The composition may be provided as a water thin liquid, structured liquid or emulsion. The composition is preferably provided as a ready to use composition, meaning that the composition is provided in a way that can be applied without needing to dilute it first.

Packaging and Dispensers

The composition may be provided in various packaging sizes. Examples of packaging sizes include 1.5 oz, 500 ml and 1 liter bottles. The selected packaging preferably has a pump head foamer. Examples of commercially available pump head foamers include the F2 foamer from Rexam PLC (London, England, formerly Airspray), and the RF-17 Palm Foamer from Rieke Corporation (Auburn, Ind.).

DEFINITIONS

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Weight percent, percent by weight, % by weight, wt %, and the like are synonyms that refer to the concentration of a substance as the weight of that substance divided by the weight of the composition and multiplied by 100.

The recitation of numerical ranges by endpoints includes all numbers subsumed within that range (e.g. 1 to 5 includes 1, 1.5, 2, 2.75, 3, 3.80, 4 and 5).

As used in this specification and the appended claims, the singular forms "a," "an," and "the" include plural referents unless the content clearly dictates otherwise. Thus, for example, reference to a composition containing "a compound" includes a mixture of two or more compounds. As used in this specification and the appended claims, the term "or" is generally employed in its sense including "and/or" unless the content clearly dictates otherwise.

For a more complete understanding of the invention, the following examples are given to illustrate some embodiment. These examples and experiments are to be understood as illustrative and not limiting. All parts are by weight, except where it is contrarily indicated.

EXAMPLES

Example 1

Silicone Surfactant Screening

Example 1 shows various silicone surfactants and their ability to generate a stable foam. The foaming ability of the silicone surfactants was evaluated using the following foam height screening procedure.

Stock Solution Preparation: A solution consisting of 75.6% Ethanol SDA 40B (190 proof, 99.5% Active) and 24.4% water was prepared.

Sample Preparation: To a 20 mL vial, approximately 0.35 g of silicone surfactant and 9.65 g Stock solution were weighed. The solution was then mixed until a homogeneous solution was achieved.

Foam Height Screening: To screen the foam height of each solution, a small portion (~1 mL) of the prepared solution was placed into a 2 oz bottle with an Airspray foaming pump head, rinsed around, and discarded. After the rinsing of the bottle, the remaining contents of the sample preparation were then transferred into the 2 oz bottle with an Airspray foaming pump head. The foaming pump head was primed until liquid or foam was generated through the foamer head. Up to three additional pumps were performed to ensure that the initial solution had been evacuated through the pump. After priming the pump, three additional pumps were performed, directing the material into a 20 mL glass vial. The height of the foam above the liquid line was immediately measured in millimeters using a ruler. The process was repeated one additional time and the two foam height measurements were averaged. The results are shown in Table 1.

TABLE 1

Silicone Surfactant Screening

| Manufacturer | Name | INCI Name | chemistry type/ structure | Avg. Foam Height (mm) |
|---|---|---|---|---|
| Noveon | Silsense CA2 | dimethicone PEG-7 succinate | pendant | 9.5 |
| Noveon | Silsense Q Plus | silicone quaternium-8 | pendant | 10.5 |
| Noveon | Silsense Copolyol 7 | PEG-33 and PEG-14 and PEG-8 dimethicone | pendant | 9 |
| Noveon | Silsense Copolyol 1 | PEG-33 and PEG-8 dimethicone and PEG-14 | pendant | 8.5 |
| Siltech | Silube CS-1 | PEG-7 dimethiconesuccinate | pendant | 6.5 |
| Siltech | Silphos A-100 | silicone polyether phosphate esters* | pendant | 5 |
| Siltech | Silsurf B-208 | PEG-8 dimethicone | pendant | 5 |
| Siltech | Silsurf A-208 | PEG-8 dimethicone | pendant | 5.5 |
| Siltech | Silsurf Di-1010 | PEG-10 dimethicone | linear | 25 |
| Siltech | Silsurf D212-CG | PEG-12 dimethicone | pendant | 9 |
| Siltech | Silquat AD | silicone quaternium-8 | pendant | 4 |
| Siltech | Silquat J208-1B | PEG-8 disteramonium chloride PG-dimethicone | pendant | 8 |
| Degussa | EM 97 | bis-PEG/PPG-14/14 dimethicone, cyclopentasiloxane | alpha, omega omega-polyethersiloxane linear | 11.5 |
| Degussa | 85 | bis-PEG/PPG-16/16 PEG/PPG-16/16 dimethicone, caprylic/capric, triglyceride | with the addition of caprylic/capric acid triglyceride linear | 15 |
| Degussa | B 8852 | PEG/PPG-4/12 dimethicone | pendant | |
| Degussa | B 8832 | bis-PEG/PPG-20/20 dimethicone | linear | 18 |
| Grant Industries | Gransurf 71 | PEG-11 methyl ether dimethicone | pendant | 9 |
| Grant Industries | Gransurf 77 | PEG-10 dimethicone | pendant | 8 |
| Waker | Waker-Belsil DMC 6031 | PEG/PPG-25/25 dimethicone | pendant | 8 |
| Waker | Waker-Belsil DMC 6038 | bis-PEG 15 methyl ether dimethicone | methyl ether endcapped linear | 3 |
| Waker | DMC3071VP | cetyl PEG/PPG-15/15 butyl ether dimethicone | pendant | 5 |
| Shin Etsu | KF-6100 | polyglyceryl-3 disiloxane dimethicone | pendant | 0 |
| Shin Etsu | KF-6017 | PEG-10 dimethicone | pendant | 12 |
| Shin Etsu | KF-6104 | polyglyceryl-3 polydimethylsixethyl diemethicone | pendant | 0 |
| Shin Etsu | KF-6028 | PEG-9 polydimethylsiloxane ethyl dimethicone | pendant | 8 |
| Shin Etsu | KF-6015 | PEG-3 dimethicone | | 0 |
| Shin Etsu | KF-6013 | PEG-9 dimethicone | pendant | 15.5 |

TABLE 1-continued

Silicone Surfactant Screening

| Manufacturer | Name | INCI Name | chemistry type/ structure | Avg. Foam Height (mm) |
|---|---|---|---|---|
| GE Silicone | Nuwet 300 | aminomodified silicone-polyether copolymer* | pendant | 11 |
| GE Silicone | L-7657 | PEG dimethicone* | pendant | 9 |
| GE Silicone | Silsoft A424 conditioner | dimethicone bisamino hydroxyethyldihydropropyl copolyol/TEA stearate | pendant | 0 |
| GE Silicone | L-7001 | siloxane polyalkyleneoxide copolymer | pendant | 5 |
| GE Silicone | Silsoft 430 dimethicone copolyol | PEG/PPG 20/23 dimethicone | pendant | 18 |
| Momentive | Silsoft 805 | PEG-8 dimethicone | pendant | 17 |
| GE Silicone | Silsoft 840 | PEG-8 dimethicone | pendant | 7.5 |
| GE Silicone | Silsoft 810 | PEG-8 dimethicone | linear | 23.5 |
| Momentive | Silsoft 870 | PEG-12 dimethicone | linear | 24.5 |
| GE Silicone | Silsoft 875 | PEG-12 dimethicone | pendant | 9 |
| GE Silicone | Silsoft 895 | PEG-17 dimethicone | pendant | 9.5 |
| Momentive | Silsoft 900 | PPG-12 dimethicone | pendant | 16.5 |
| Momentive | 1188 01P | dimethicone copolyol | pendant | 10.5 |
| Momentive | 1288 01P | dimethicone copolyol | pendant | 13 |
| Rita | Ritasil SP100S | PEG-12 dimethicone | pendant | 17 |
| Rita | Ritasil SW3050 | cetyl PEG-PPG 10/1 dimethicone | pendant | 0 |
| Clariant | Silcare Silicone SEA | trideceth-9 PG amodimethicone (and) trideceth-12 | pendant | 1 |
| Biosil | Biosil Basics SPQ | silicone quaternium-2 panthenol succinate | pendant | 3.5 |
| Biosil | Biosil Basics DL-30 | dmethiconol pnthenol | pendant | 0 |
| Biosil | Bioplex Cetyl Sil S | cetyl triethylmonium dimethicone PEG-8 succinate | pendant | 4 |
| Pheonix chemical | DCF-12 | PEG-12 dimethicone | pendant | 6 |

*no INCI name has been given for the polymers

Table 1 shows that only the linear dimethicones are able to produce a foam height greater than 20 mm. Exemplary dimethicone surfactants in Table 1 with a foam height of greater than 20 mm include Silsurf DI-1010 from Siltech, Silsoft 810 from GE Silicone, and Silsoft 870 from Momentive.

Example 2

Foam Height vs. Silicone Surfactant Concentration

Example 2 determined the effect of dimethicone surfactant concentration on the foam height. For this example, the foam height was measured using the following test:

Stock Solution Preparation: A solution was prepared with the following formula:

| Stock Solution | (g) |
|---|---|
| Ethanol SDA 40 B (190 Proof, 99.5% Active) | 811.11 |
| Farnesol | 2.78 |
| Bisabolol | 1.11 |
| Ethylhexyl glycerin | 3.33 |
| Water | 181.67 |

The following amounts were added to 60 mL jars. The silicone surfactants used were Silsurf DI-1010, Silsoft 810, and Silsoft 870.

Sample Preparation: To a 60 mL jar,

| Sample | 1 | 2 | 3 | 4 | 5 | 6 | 7 |
|---|---|---|---|---|---|---|---|
| Stock solution (g) | 22.500 | 45.00 | 45.00 | 45.00 | 45.00 | 45.00 | 45.00 |
| Silicone surfactant (g) | 0.125 | 0.50 | 1.00 | 1.50 | 1.75 | 2.50 | 5.00 |
| Silicone surfactant (wt. %) | 0.5 | 1 | 2 | 3 | 3.5 | 5 | 10 |
| Water (g) | 2.375 | 4.50 | 4.00 | 3.50 | 1.25 | 2.50 | 0.00 |

Foam Height Screening: To screen the foam height of each solution, a small portion (~1 mL) of the prepared solution was used to rinse a 2 oz bottle with an Airspray foaming pump head and discarded. After rinsing the bottle, the remaining contents of the sample preparation were then transferred into the 2 oz bottle with an Airspray foaming pump head. The foaming pump head was primed until liquid or foam was generated through the foamer head. Up to three additional pumps were performed to ensure that the rinse solution had been evacuated through the pump. After priming the pump, three additional pumps were performed, directing the material into a 20 mL glass vial. The height of the foam above the liquid line was immediately measured in millimeters using a ruler. The process was repeated and the two foam height measurements were averaged. The results are shown in Table 2.

TABLE 2

| Sample | Foam Height (mm) | | | | | | |
|---|---|---|---|---|---|---|---|
| | 1 | 2 | 3 | 4 | 5 | 6 | 7 |
| Silsoft 810 | 12 | 11.5 | 20 | 24 | 25.5 | 26 | 26 |
| Silsurf DI-1010 | 14.5 | 22.5 | 23.5 | 24 | 25 | 26 | 26.5 |
| Silsoft 870 | 13 | 17 | 23.5 | 25.5 | 26 | 26 | 27 |

Table 2 shows that 0.5-1 gram of silicone surfactant (samples 2 and 3) is preferred in order to generate 20 mm of foam.

The foregoing summary, detailed description, and examples provide a sound basis for understanding the invention, and some specific example embodiments of the invention. Since the invention can comprise a variety of embodiments, the above information is not intended to be limiting. The invention resides in the claims.

What is claimed is:

1. A non-aerosol foaming antimicrobial composition comprising:
   a) a foaming agent comprising a PEG-8 linear dimethicone surfactant;
   b) a $C_2$ to $C_4$ alcohol; and
   c) water.

2. The composition of claim 1 wherein said $C_2$ to $C_4$ alcohol is in an amount of from about 50 wt. % to about 90 wt. % of said composition.

3. The antimicrobial composition of claim 1, further comprising from about 0.01 to about 20 wt. % of a skin conditioner.

4. The antimicrobial composition of claim 1, wherein the composition is free of an additional surfactant.

5. The antimicrobial composition of claim 1, further comprising from about 0.005 to about 5 wt. % of a terpenoid.

6. The antimicrobial composition of claim 4, wherein said skin conditioner is selected from the group consisting of ethylhexylglycerin, hydroxyethylurea, urea, panthenol, glycerin, isopropyl myristate, propylene glycol, tocopheryl acetate, polyquaternium-11 and mixtures thereof.

7. A non-aerosol foaming antimicrobial composition comprising:
   a) a foaming agent comprising a PEG-10 linear dimethicone surfactant;
   b) a $C_2$ to $C_4$ alcohol; and
   C) water.

8. The composition of claim 7 wherein said $C_2$ to $C_4$ alcohol is in an amount of from about 50 wt. % to about 90 wt. % of said composition.

9. The antimicrobial composition of claim 7, further comprising from about 0.01 to about 20 wt. % of a skin conditioner.

10. The antimicrobial composition of claim 7, wherein the composition is free of an additional surfactant.

11. The antimicrobial composition of claim 7, further comprising from about 0.005 to about 5 wt. % of a terpenoid.

12. The antimicrobial composition of claim 11, wherein said skin conditioner is selected from the group consisting of ethylhexylglycerin, hydroxyethylurea, urea, panthenol, glycerin, isopropyl myristate, propylene glycol, tocopheryl acetate, polyquaternium-11 and mixtures thereof.

13. An alcohol containing antimicrobial foaming composition comprising a PEG-8 or PEG-10 linear silicone surfactant foaming agent.

14. The antimicrobial composition of claim 13, wherein said composition is a liquid emulsion.

15. The antimicrobial composition of claim 13, wherein said composition is a ready to use composition.

16. The antimicrobial composition of claim 13, wherein said composition is a structured liquid composition.

17. The antimicrobial composition of claim 13, wherein said composition is a water thin liquid composition.

* * * * *